US010039705B1

(12) United States Patent
Lee et al.

(10) Patent No.: US 10,039,705 B1
(45) Date of Patent: Aug. 7, 2018

(54) SUN PROTECTION MATERIAL AND SUN PROTECTION COMPOSITION CONTAINING THE SAME

(71) Applicant: National Tsing Hua University, Hsinchu (TW)

(72) Inventors: Chi-Young Lee, Hsinchu (TW); Hsin-Tien Chiu, Hsinchu (TW); Min-Chiao Tsai, Tainan (TW); Kuei-Lin Chan, Hsinchu (TW); Shao-Gang Cheng, Yunlin County (TW); Yi-Hsuan Chen, Taipei (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 15/581,682

(22) Filed: Apr. 28, 2017

(51) Int. Cl.
| | | |
|---|---|---|
| *A61K 8/29* | (2006.01) | |
| *A61K 8/81* | (2006.01) | |
| *A61K 8/02* | (2006.01) | |
| *A61Q 17/04* | (2006.01) | |

(52) U.S. Cl.
CPC ............ *A61K 8/8117* (2013.01); *A61K 8/025* (2013.01); *A61K 8/29* (2013.01); *A61Q 17/04* (2013.01); *A61K 2800/413* (2013.01)

(58) Field of Classification Search
CPC ....................................................... A61K 8/29
See application file for complete search history.

(56) References Cited

U.S. PATENT DOCUMENTS

| 2008/0268002 A1 | 10/2008 | Dumousseaux et al. |
| 2013/0084318 A1* | 4/2013 | Ghosh Dastidar ... A61K 8/0279 424/401 |
| 2016/0250110 A1 | 9/2016 | Hudelist et al. |

FOREIGN PATENT DOCUMENTS

| CN | 101077792 | 11/2007 |
| TW | 200846027 | 12/2008 |

OTHER PUBLICATIONS

Imhof (Langmuir 2001, 17, 3579-3585).*
Feng Lin,"Preparation and Characterization of Polymer TiO2 Nanocomposites via In-situ Polymerization", A thesis presented to the University of Waterloo in fulfillment of the thesis requirement of the degree of Master of Applied Science in Chemical Engineering, 2006, pp. 1-160.
Dina Fattakhova-Rohlfing et al.,"Three-Dimensional Titanium Dioxide Nanomaterials", Chemical Reviews, vol. 114, No. 19, Aug. 19, 2014, pp. 9487-9558.

* cited by examiner

*Primary Examiner* — Benjamin J Packard
(74) *Attorney, Agent, or Firm* — J.C. Patents

(57) ABSTRACT

Provided is a sun protection material including a plurality of polystyrene microspheres and a plurality of refractive layers. The polystyrene microspheres have a particle size of 150 nm to 300 nm. Surfaces of the polystyrene microspheres are at least partially covered by the refractive layers. The sun protection material can scatter a light in a wavelength range between 250 nm and 400 nm. A sun protection composition containing the sun protection material also may scatter a light of a wavelength range between 250 nm and 400 nm, such that the UV protection of the sun protection composition is enhanced.

11 Claims, 5 Drawing Sheets

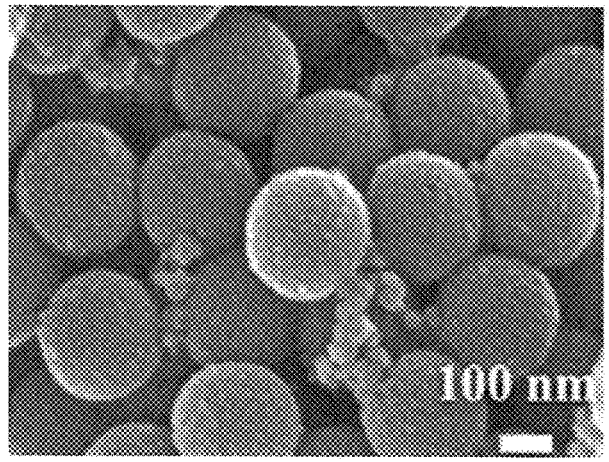
FIG. 4
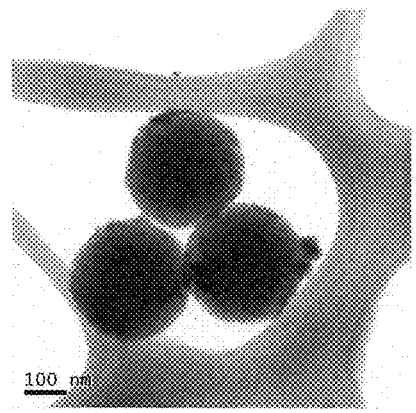 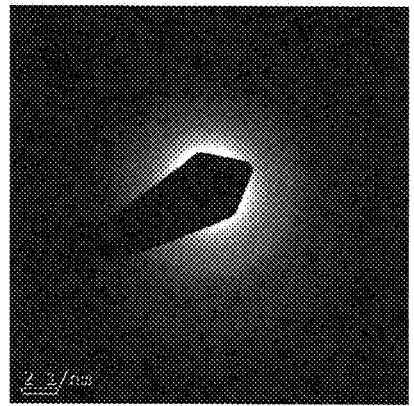
FIG. 5A  FIG. 5B

SUN PROTECTION MATERIAL AND SUN PROTECTION COMPOSITION CONTAINING THE SAME

BACKGROUND OF THE INVENTION

1. Field of the Invention

The invention relates to a sun protection material, and more particularly, to a sun protection composition containing the sun protection material.

2. Description of Related Art

UV causes damages such as sun burn and sun tan to the human skin, and can even cause, for instance, skin cancer. UV in sunlight can be categorized into three groups according to the wavelength: long-wave UV (UVA), medium-wave ultraviolet (UVB), and short-wave UV (UVC). In particular, UVA has very strong penetration power, and can reach the dermal layer of the skin, thus facilitating aging of the skin, even causing skin cancer. UVA causes chronic and long-term damage to the skin, and since UVA has the highest proportion in the components of UV in sunlight, sun protection is even more important.

Due to increased demand for sun protection, the medical and beauty industries have flourished in recent years. In general, sun protection principles are divided into two broad categories: physical sun protection and chemical sun protection. Physical sun protection blocks UV with the principle of using a sunscreen to reflect or scatter light. In chemical sun protection, UV is absorbed by using a chemical substance to convert the chemical substance into molecular vibrational energy or heat energy to eliminate UV damage.

Although many international manufacturers continuously develop new sun protection products, the sun protection efficacy of physical sun protection cannot be significantly enhanced. Both the market and the industry emphasize the nanonization of a physical sunscreen to prevent excessively white makeup; however, the nanonization of the physical sunscreen cannot provide better UV protection capability, and instead the usage amount of the physical sunscreen or the chemical sunscreen needs to be increased. However, the nanoparticles in the physical sunscreen may increase the difficulty of dispersion of a powder in an emulsion, and may also cause the potential risk of being inhaled into the body; and an increase in the chemical sunscreen causes damage to the skin.

SUMMARY OF THE INVENTION

The invention provides a sun protection material and a sun protection composition containing the sun protection material capable of scattering light in a wavelength range between 250 nm and 400 nm, such that the UV protection capability of the sun protection composition is enhanced.

The invention provides a sun protection material including a plurality of polystyrene microspheres and a plurality of refractive layers. The polystyrene microspheres have a particle size of 150 nm to 300 nm. Surfaces of the polystyrene microspheres are at least partially covered by the refractive layers. The sun protection material can scatter a light in a wavelength range between 250 nm and 400 nm.

In an embodiment of the invention, the refractive layers include titanium dioxide, zinc oxide, silicon oxide or a combination thereof.

In an embodiment of the invention, the refractive layers are amorphous.

In an embodiment of the invention, a refractive index of the refractive layers is greater than a refractive index of the polystyrene microspheres.

In an embodiment of the invention, the surfaces of the polystyrene microspheres are completely covered by the refractive layers.

In an embodiment of the invention, the polystyrene microspheres are solid microspheres.

In an embodiment of the invention, a ratio of a long diameter and a short diameter of each of the polystyrene microspheres is between 1.03 and 1.07.

In an embodiment of the invention, a difference of any two diameters of the polystyrene microspheres is less than 20 nm.

In an embodiment of the invention, the difference of any two diameters of the polystyrene microspheres is between 6.8 nm and 15.2 nm.

In an embodiment of the invention, the standard deviation of the particle size distribution of polystyrene microspheres is less than 2.35 nm.

The invention provides a sun protection composition including the above mentioned sun protection material and a UV absorbent. Based on 100 wt % of the sun protection composition, a content of the sun protection material is 0 wt % to 10 wt %.

In an embodiment of the invention, the sun protection composition has an SPF value of at least 50.

Based on the above, the sun protection material of the invention has polystyrene microspheres having a particle size of 150 nm to 300 nm, such that the sun protection material can scatter light in a wavelength range between 250 nm and 400 nm. In addition, the refractive layers having the refractive index more than the refractive index of the polystyrene microspheres at least partially cover the surfaces of the polystyrene microspheres, so as to enhance the ability of refracting light in a wavelength range between 250 nm and 400 nm. Therefore, the sun protection composition containing the sun protection material can scatter light in a wavelength range between 250 nm and 400 nm, such that the UV protection capability of the sun protection composition is enhanced.

In order to make the aforementioned features and advantages of the disclosure more comprehensible, embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 4 is an electron micrograph of experimental example 4.

FIG. 5A is a transmission electron microscopy (TEM) image of experimental example 4.

FIG. 5B is an electron diffraction image of experimental example 4.

DESCRIPTION OF THE EMBODIMENTS

Figure 1:
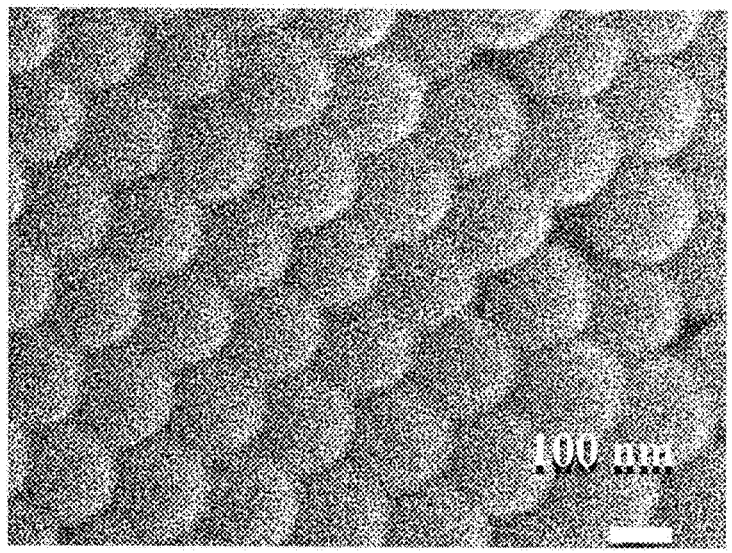
FIG. 1 is an electron micrograph of experimental example 1.

Reference will now be made in detail to the present preferred embodiments of the invention, examples of which are illustrated in the accompanying drawings. Wherever possible, the same reference numbers are used in the drawings and the description to refer to the same or like parts.

In the present specification, ranges represented by "a numerical value to another numerical value" are schematic representations to avoid listing all of the numerical values in the range in the specification. Therefore, the recitation of a specific numerical range discloses any numerical value in the numerical range and a smaller numerical range defined by any numerical value in the numerical range, as is the case with any numerical value and a smaller numerical range stated expressly in the specification. For instance, the range of "a particle size of 150 nm to 300 nm" discloses the range of "a particle size of 200 nm to 250 nm", regardless of whether other numerical values are listed in the specification.

The invention provides a sun protection material including a plurality of polystyrene microspheres and a plurality of refractive layers. In an embodiment, the polystyrene microspheres are solid microspheres, for example. The shape of the polystyrene microspheres may be circle, such as a perfect circle or a rough circle, and the size is uniform. The particle size of the polystyrene microspheres is, for instance, 150 nm to 300 nm. The circle or the rough circle here implies that the ratio of the long diameter and the short diameter of every polystyrene microsphere is substantially close to 1. In an embodiment, the ratio of the long diameter and the short diameter of every polystyrene microsphere is 1.03 to 1.07. In some embodiments, the difference of any two diameters of the polystyrene microspheres is less than 20 nm. In alternative embodiment, the difference of any two diameters of the polystyrene microspheres is between 6.8 nm and 15.2 nm. In another embodiment, the standard deviation of the particle size distribution of polystyrene microspheres is less than 2.35 nm. The polystyrene microspheres can scatter light in a wavelength range between 250 nm and 400 nm. The scattering properties allow the sun protection material of the invention to have high extinction capability, such as scattering, absorption or a combination thereof, for UV wave bands such that the sun protection material can effectively improve the existing physical and chemical sunscreen, and thereby increase UV blocking capability. In the invention, the polystyrene microspheres having uniform size and good dispersibility (monodispersed) can be synthesized by emulsifier-free emulsion polymerization. Styrene is mixed with the initiator, 2,2'-Azobis(2-methylpropionamidine) dihydrochloride (AIBA) and the stabilizer, Polyvinylpyrrolidone (PVP) and react for 18 hours at about 70° C. Under suitable parameter regulations, the particle size of the polystyrene microspheres can be adjusted. By adjusting the particle size of the polystyrene microspheres, the UV-visible light extinction spectrum thereof can be further regulated.

When the particle size of the polystyrene microspheres of the invention is between 150 nm and 300 nm, especially in 240 nm, strong scattering occurs at UVB (280 nm to 315 nm) and UVA (315 nm to 400 nm) wave bands. Therefore, the polystyrene microspheres of the invention have better protection capability against UVA and UVB readily causing skin tan, sun burn, or even skin cancer.

In addition, the surfaces of the polystyrene microspheres are at least partially covered by the refractive layers. In some embodiments, the refractive index of the refractive layers is greater than the refractive index of the polystyrene microspheres. Therefore, the refractive layers covered the surfaces of the polystyrene microspheres are able to enhance the ability of refracting light in a wavelength range between 250 nm and 400 nm. For instance, the refractive index of the polystyrene microspheres may be 1.59, and the refractive index of the refractive layers may be between 2.0 and 2.4. In an embodiment, the refractive layers include titanium dioxide, zinc oxide, silicon oxide or a combination thereof. In some embodiments, the refractive layers may be amorphous, namely, the refractive layers may not have crystalline phase. In alternative embodiment, the refractive layers completely cover the surfaces of the polystyrene microspheres.

In another embodiment, the sun protection material may be applied or used in a cosmetic to enhance the UV protection capability of the cosmetic. More specifically, the sun protection composition includes the foregoing sun protection material. The content of the sun protection material is 0 wt % to 10 wt %. The contents described here refer to weight percentages of each component to the overall sun protection composition. In some embodiments, the sun protection composition containing the foregoing sun protection material has a sun protection factor (SPF) value of at least 50. Therefore, the sun protection composition containing the foregoing sun protection material has better protection capability against UV of UVB wave band.

A plurality of experimental examples is provided below to further describe the sun protection material and the sun protection material composition of the invention. In the following, the degree of extinction for a wavelength of 200 nm to 800 nm was tested with an UV-vis spectrophotometer (e.g., AvaSpec-2048 UV spectrum).

Figure 2:
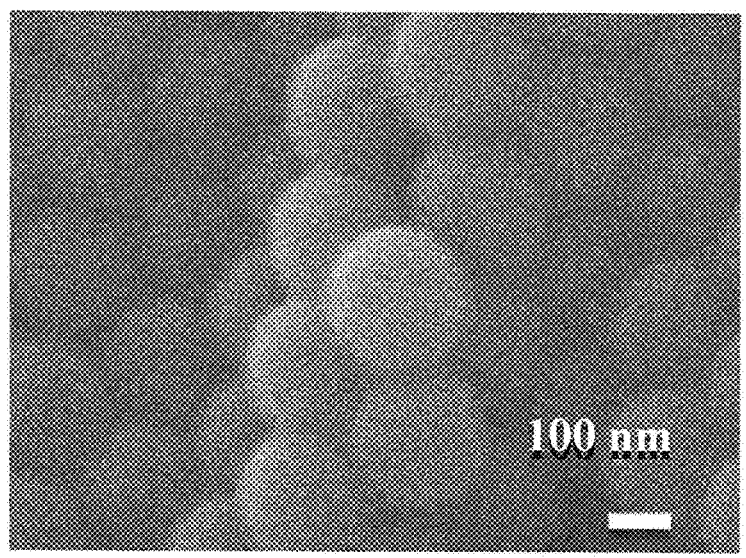
FIG. 2 is an electron micrograph of experimental example 2.

FIG. 1 is an electron micrograph of experimental example 1. FIG. 2 is an electron micrograph of experimental example 2.

Experimental Example 1

Figure 3:
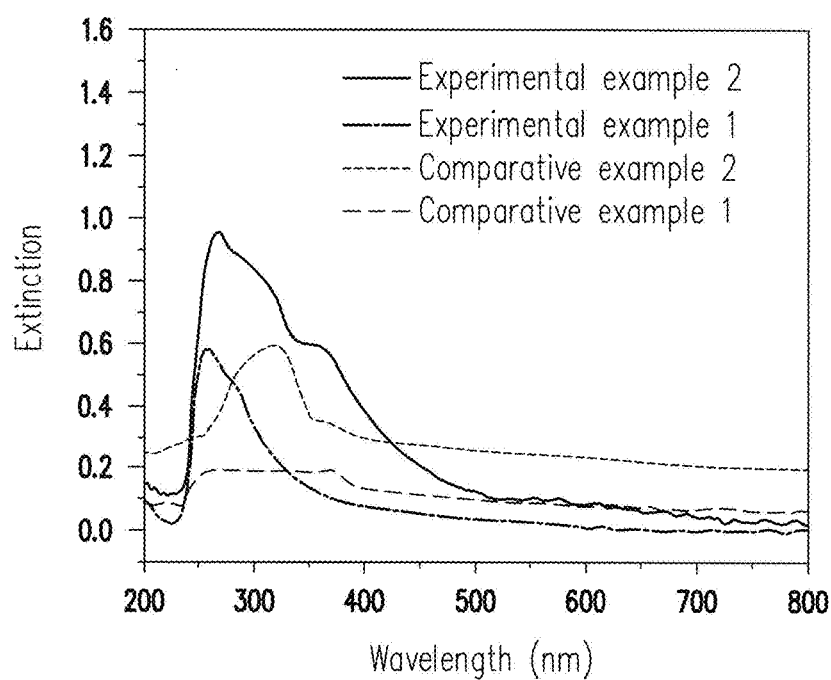
FIG. 3 is the UV-visible light extinction spectra of experimental examples 1 to 2 and comparative examples 1 to 2.

In experimental example 1, the polystyrene microspheres having a particle size of 180 nm were synthesized by emulsifier-free emulsion polymerization. Specifically, 25 g styrene is mixed with 0.65 g AIBA and 3.75 g PVP and react for 18 hours at about 70° C. The Scanning Electron Microscopy (SEM) result of the polystyrene microspheres having the particle size of 180 nm is as shown in FIG. 1. Then, the polystyrene microspheres having a concentration of 1 wt % were spin coated on a quartz glass, and a UV-visible light extinction spectrum test was performed by using an UV-vis spectrophotometer. The result thereof is as shown in FIG. 3.

Experimental Example 2

In experimental example 2, the polystyrene microspheres having a particle size of 240 nm were synthesized by emulsifier-free emulsion polymerization. Specifically, 50 g styrene is mixed with 1.3 g AIBA and 7.5 g PVP and react for 18 hours at about 70° C. The SEM result of the polystyrene microspheres having the particle size of 240 nm is as shown in FIG. 2. Then, the polystyrene microspheres having a concentration of 1 wt % were spin coated on a quartz glass, and a UV-visible light extinction spectrum test was performed by using an UV-vis spectrophotometer. The result thereof is as shown in FIG. 3.

As shown in FIGS. 1 to 2, the shape of the polystyrene microspheres of experimental examples 1-2 is circle and the size is uniform. In addition, the standard deviation of the particle size distribution of polystyrene microspheres of Experimental examples 1 is about 2.04 nm, and of Experimental examples 2 is about 2.29 nm. When the particle size of the polystyrene microspheres of the invention is between 150 nm and 300 nm, strong scattering occurs at UVB (280 nm to 315 nm) and UVA (315 run to 400 nm) wave bands. Therefore, the polystyrene microspheres of experimental examples 1-2 have better protection capability against UVA and UVB.

FIG. 3 is the UV-visible light extinction spectra of experimental examples 1 to 2 and comparative examples 1 to 2.

Comparative Example 1

In comparative example 1, 1 wt % of zinc oxide (product of UV ESSENTIEL, available by CHANEL) was used. UV-visible light extinction spectrum test was then performed by using the UV-vis spectrophotometer. The result is as shown in FIG. 3.

Comparative Example 2

In comparative example 1, 1 wt % of zinc oxide (product of UV ESSENTIEL, available by CHANEL) is mixed with 2.5 wt % of the UV absorbent (product of Uvinul, model: MC 80, available by BASF) was used. UV-visible light extinction spectrum test was then performed by using the UV-vis spectrophotometer. The result is also as shown in FIG. 3.

The results of FIG. 3 show that, the degree of extinction of the polystyrene microspheres having the particle size of 240 nm of experimental example 2 at UVB (280 nm to 315 nm) and UVA (315 nm to 400 nm) wave bands is much greater than that of the commercial zinc oxide of comparative examples 1 to 2. In other words, experimental example 2 has better protection capability against UV at UVA and UVB wave bands.

Figure 6:
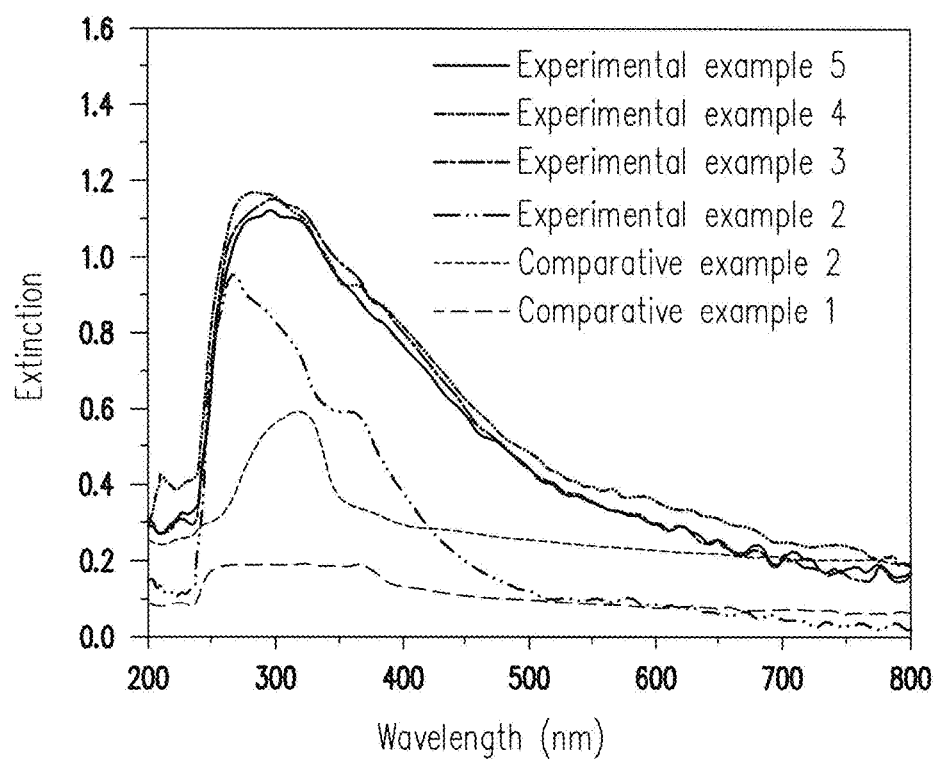
FIG. 6 is the UV-visible light extinction spectra of experimental examples 2 to 5 and comparative examples 1 to 2.

FIG. 4 is an electron micrograph of experimental example 4. FIG. 5A is a transmission electron microscopy (TEM) image of experimental example 4. FIG. 5B is an electron diffraction image of experimental example 4. FIG. 6 is the UV-visible light extinction spectra of experimental examples 2 to 5 and comparative examples 1 to 2.

Experimental Example 3

In experimental example 3, the polystyrene microspheres of experimental example 2 coated by titanium dioxide (PS@TiO$_2$) were synthesized by using a sol-gel method. Specifically, 3% of the polystyrene microspheres of experimental example 2 used as templates are mixed with 0.3% of titanium isopropoxide (TTIP) to form PS@TiO$_2$ microspheres at room temperature (about 25° C.). Then, 1 wt % of the PS@TiO$_2$ microspheres of experimental example 3 were spin coated on a quartz glass, and a UV-visible light extinction spectrum test was performed by using an UV-vis spectrophotometer. The result thereof is as shown in FIG. 6.

Experimental Example 4

The difference between experimental example 4 and experimental example 3 is that, a content of titanium isopropoxide (TTIP) is 0.9% in experimental example 4. The SEM result of PS@TiO$_2$ microspheres of experimental example 4 is as shown in FIG. 4. The TEM result of PS@TiO$_2$ microspheres of experimental example 4 is as shown in FIG. 5A. Then, 1 wt % of the PS@TiO$_2$ microspheres of experimental example 3 were spin coated on a quartz glass, and a UV-visible light extinction spectrum test was performed by using an UV-vis spectrophotometer. The result thereof is as shown in FIG. 6.

As shown in FIGS. 4 and 5A, the surfaces of the polystyrene microspheres are partially coated or covered by the TiO$_2$. As shown in FIG. 5B, the PS@TiO$_2$ microspheres of experimental example 4 are amorphous, namely, the PS@TiO$_2$ microspheres of experimental example 4 do not have crystalline phase. Therefore, the PS@TiO$_2$ microspheres of the invention are able to add into the cosmetic without causing damage to the skin of human being.

Experimental Example 5

The difference between experimental example 5 and experimental example 3 is that, a content of titanium isopropoxide (TTIP) is 1.5% in experimental example 5. 1 wt % of the PS@TiO$_2$ microspheres of experimental example 5 were spin coated on a quartz glass, and a UV-visible light extinction spectrum test was performed by using an UV-vis spectrophotometer. The result thereof is as shown in FIG. 6.

The results of FIG. 6 show that, the degree of extinction of PS@TiO$_2$ microspheres of experimental examples 3 to 5 at UVB (280 nm to 315 nm) and UVA (315 nm to 400 nm) wave bands is much greater than that of the commercial zinc oxide of comparative examples 1 to 2 and pure polystyrene microspheres of experimental example 2. In other words, PS@TiO$_2$ microspheres are able to enhance the ability of refracting light in a wavelength range between 250 nm and 400 nm of the pure polystyrene microspheres, such that the PS@TiO$_2$ microspheres have better protection capability against UV at UVA and UVB wave bands.

Figure 7:
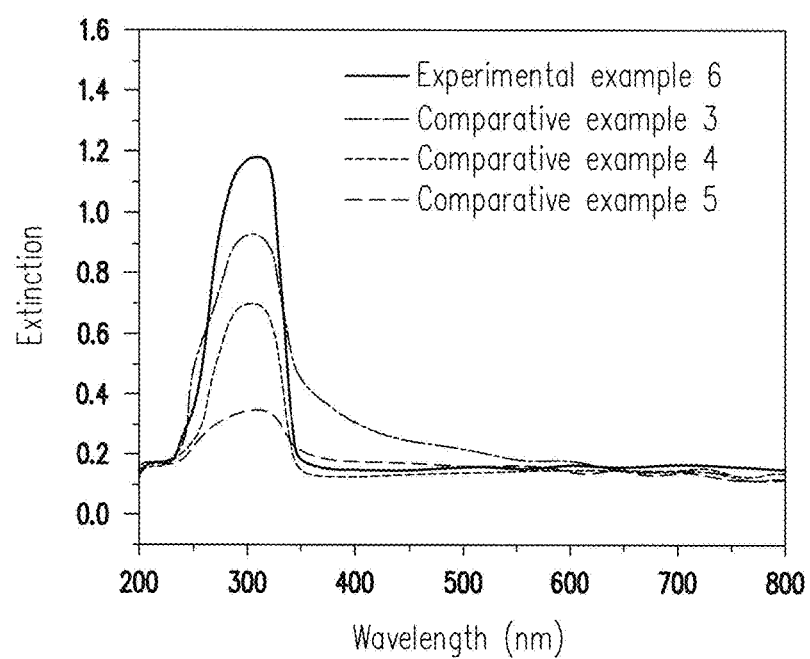
FIG. 7 is the UV-visible light extinction spectra of experimental example 6 and comparative examples 3 to 5.

FIG. 7 is the UV-visible light extinction spectra of experimental example 6 and comparative examples 3 to 5.

Experimental Example 6

2 wt % of PS@TiO$_2$ microspheres of experimental example 4 is mixed with sodium acrylate, aloe extract, tocopheryl acetate, isobexadecane, propylene glycol, water, rose volatile oil and zemea to form a cosmetic having sun protection efficacy. The content of TiO$_2$ adding in the cosmetic of experimental example 6 is as shown in Table 1. Then, the cosmetic of experimental example 6 is coated on a surface of a glass substrate layer by layer. A sun protection factor (SPF) test was performed on the cosmetic of experimental example 6 on the glass substrate. The result thereof is as shown in Table 2. Next, 100 wt % of the cosmetic of experimental example 6 was smeared on a quartz glass uniformly, and a UV-visible light extinction spectrum test was performed by using an UV-vis spectrophotometer. The result thereof is as shown in FIG. 7.

Comparative Examples 3 to 5

The difference between comparative examples 3 to 5 and experimental example 6 is that in comparative examples 3 to 5, different commercial titanium dioxides were respectively used to perform the SPF test and the UV-visible light extinction spectrum test, and the test method thereof is the same as that of experimental example 6. Specifically, in comparative example 3, a titanium dioxide pigment (model: F-XT, available by Bauwei Cosmetic) having a concentration of 10 wt % was used. In comparative example 4, a titanium dioxide pigment (model: F-YS, available by Bauwei Cosmetic) having a concentration of 8 wt % was used. In comparative example 5, a titanium dioxide pigment (model: D-M1, available by DuPont) having a concentration of 2 wt % was used. The content of $TiO_2$ adding in the cosmetic of comparative examples 3 to 5 are as shown in Table 1. UV-visible light extinction spectrum tests were respectively performed by using the UV-vis spectrophotometer. The results are as shown in FIG. 6.

TABLE 1

| Test Item | Content of $TiO_2$ |
| --- | --- |
| Experimental example 6 | 2% |
| Comparative example 3 | 10% |
| Comparative example 4 | 8% |
| Comparative example 5 | 2% |

It can be known from Table 1 that, compared with the cosmetic of comparative examples 3 to 5, the cosmetic of experimental example 6 has less content $TiO_2$.

TABLE 2

| Test Item | SPF value |
| --- | --- |
| Experimental example 6 | 50+ |
| Comparative example 3 | 28~35 |
| Comparative example 4 | |

The results of FIG. 7 show that, the degree of extinction of PS@$TiO_2$ microspheres of experimental examples 6 at UVB (280 nm to 315 nm) and UVA (315 nm to 400 nm) wave bands is much greater than that of the commercial zinc oxide of comparative examples 3 to 5. In other words, the cosmetic containing PS@$TiO_2$ microspheres in experimental example 6 has better protection capability against UV at UVA and UVB wave bands.

Based on the above, the sun protection material of the invention has polystyrene microspheres having a particle size of 150 nm to 300 nm, such that the sun protection material can scatter light in a wavelength range between 250 nm and 400 nm. In addition, the refractive layers having the refractive index more than the refractive index of the polystyrene microspheres at least partially cover the surfaces of the polystyrene microspheres, so as to enhance the ability of refracting light in a wavelength range between 250 nm and 400 nm. Therefore, the sun protection composition containing the sun protection material can scatter light in a wavelength range between 250 nm and 400 nm, such that the UV protection capability of the sun protection composition is enhanced.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A sun protection material, comprising:
    a plurality of polystyrene microspheres having a particle size of 150 nm to 300 nm; and
    a plurality of refractive layers at least partially covering surfaces of the polystyrene microspheres, wherein the sun protection material scatters a light in a wavelength range between 250 nm and 400 nm, wherein a refractive index of the refractive layers is greater than a refractive index of the polystyrene microspheres.

2. The sun protection material according to claim 1, wherein the refractive layers comprise titanium dioxide, zinc oxide, silicon oxide or a combination thereof.

3. The sun protection material according to claim 1, wherein the refractive layers are amorphous.

4. The sun protection material according to claim 1, wherein the refractive layers completely cover the surfaces of the polystyrene microspheres.

5. The sun protection material according to claim 1, wherein the polystyrene microspheres are solid microspheres.

6. The sun protection material according to claim 1, wherein a ratio of a long diameter and a short diameter of each of the polystyrene microspheres is between 1.03 and 1.07.

7. The sun protection material according to claim 1, wherein a difference of any two diameters of the polystyrene microspheres is less than 20 nm.

8. The sun protection material according to claim 1, wherein a difference of any two diameters of the polystyrene microspheres is between 6.8 nm and 15.2 nm.

9. The sun protection material according to claim 1, wherein the standard deviation of the particle size distribution of polystyrene microspheres is less than 2.35 nm.

10. A sun protection composition, comprising:
    the sun protection material of claim 1, wherein a content of the sun protection material is 0 wt % to 10 wt % based on 100 wt % of the sun protection composition.

11. The sun protection composition of claim 10, wherein the sun protection composition has an SPF value of at least 50.

* * * * *